US006613051B1

(12) United States Patent
Luk et al.

(10) Patent No.: US 6,613,051 B1
(45) Date of Patent: Sep. 2, 2003

(54) ANTERIOR TRANSPEDICULAR FIXATION SYSTEM AND METHOD FOR MAINTAINING A VERTEBRAL COLUMN

(75) Inventors: Dip Kei Luk, Hong Kong (CN); Weijia Lu, Hong Kong (CN); Duo Sai Lu, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 50 days.

(21) Appl. No.: 09/714,927

(22) Filed: Nov. 17, 2000

Related U.S. Application Data
(60) Provisional application No. 60/165,971, filed on Nov. 17, 1999.

(51) Int. Cl.[7] .............................................. A61B 17/56
(52) U.S. Cl. ........................ 606/61; 606/73; 623/17.11
(58) Field of Search ............................. 606/60, 61, 66, 606/69–73; 623/16.11, 17.11, 17.15, 17.16

(56) References Cited

U.S. PATENT DOCUMENTS

| | | | | |
|---|---|---|---|---|
| 4,648,388 A | * | 3/1987 | Steffee ..................... 248/316.6 |
| 5,000,166 A | * | 3/1991 | Karpf ........................... 606/61 |
| 5,147,361 A | * | 9/1992 | Ojima et al. .................. 606/61 |
| 5,180,381 A | * | 1/1993 | Aust et al. .................... 606/61 |
| 5,324,290 A | | 6/1994 | Zdeblick et al. ............... 606/61 |
| 5,395,371 A | * | 3/1995 | Miller et al. ................... 606/61 |
| 5,395,372 A | | 3/1995 | Holt et al. ..................... 606/61 |
| 5,616,144 A | * | 4/1997 | Yapp et al. .................... 606/61 |
| 5,653,710 A | * | 8/1997 | Harle ............................ 606/61 |
| 5,728,097 A | * | 3/1998 | Mathews ....................... 606/61 |

FOREIGN PATENT DOCUMENTS

| | | | |
|---|---|---|---|
| EP | 0 284 530 | * 9/1988 | |
| EP | 0 574 098 | 12/1993 | ............. A61F/2/30 |

* cited by examiner

*Primary Examiner*—Michael Peffley
(74) *Attorney, Agent, or Firm*—Robert D. Katz; Cooper & Dunham LLP

(57) ABSTRACT

The present invention relates to an internal anterior transpedicular fixation system and a method for rigidly fixing the spine anteriorly at the level above and below a thoracolumbar burst fracture or tumor. The internal anterior transpedicular fixation system has a support member defining a plurality of engaging portions thereon. At least two of the engaging portions are spaced longitudinally from each other and adapted to span at least one verteba. At least two of the engaging portions are spaced laterally from each other and adapted to span a lateral distance of the verteba. A plurality of fixation elements are provided to mount the engaging portions onto the verteba. Thereby, the support member is restrained from rotational or translational movement relative to the verteba.

18 Claims, 5 Drawing Sheets

ANTERIOR TRANSPEDICULAR FIXATION SYSTEM AND METHOD FOR MAINTAINING A VERTEBRAL COLUMN

This application claims the benefit of provisional application Ser. No. 60/165,971 filed Nov. 17, 1999.

FIELD OF THE INVENTION

The present invention generally relates to a system for correcting spinal deformities anteriorly. More specifically, the present invention relates to an improved anterior transpedicular fixation system and a method for maintaining vertebrae in a desired symmetrical spatial relationship.

BACKGROUND OF THE INVENTION

Various forms of instrumentation and procedures are known for surgical treatments of spinal disorders, burst fractures, or tumors. For example, Harrington posterior Spinal Instrumentation, Edwards Hooks and Rod Sleeves, Luque Segmental Spinal Instrumentation and Luque Rectangles, and Kostuik-Harrington Instrumentation are commonly used. U.S. Pat. Nos. 4,433,676; 4,653,481; 4,269,178; 4,409,968; and 4,648,388 disclose details of such instrumentations. Some of the above systems utilize hook-type members which are merely hooked over the laminae or on selected transverse processes of the spine. Other systems, such as the Luque Segmental Spinal Rectangles which is used to stabilize spinal fractures and low back fusions, use Luque wires to secure the rectangle to the spine.

In some of the prior posterior spinal fixation systems, screws are used to hold a single rod in place. In other systems, screws are used to hold a slotted plate in place. The screws and slots are located so that the plate can be adjusted in order to align the plate apertures or slots with the end of the screw. Typically, a nut is used to hold the plate to the screw. The latter arrangement is also referred to as a Steffee plate, which is a posterior fixation system with the cantilever arrangement. Such a arrangement has the large moments applied to the plate and screw junction, but has little purchase between the plate and the screw and nut since only a small portion of the plate is engaged adjacent to the slots. In addition, the rigid plates is not flexible in locating the fasteners in the vertebrae. The above posterior approaches, even to this level of advancement, do not solve the problem of treating thoracolumbar tumors or burst fractures.

In the early 1980's various anterior fixation devices were developed to allow visualization of bone fragments that were present with burst fractures, so that attention could then be directed toward complete decompression of the canal to provide the best environment for neurological recovery. However, the anterior approach has caused increased operative morbidity due to the very difficult nature of the procedure. Moreover, many of the anterior fixation approaches have problems of potential risk to the vascular network and in complete clearance of the spinal canal. The conventional anterior approaches are not true anterior fixation but anteolateral fixations. Most of the anterior systems rely on support from the vertebral body only and therefore cannot be used in the extremely osteoporotic spine because the vertebral body strength is not sufficient.

One such system is the Kanada device marketed by Acromed, Inc. of Cleveland, Ohio. The Kanada device utilizes vertebral body staples through which fixation screws are placed into the vertebral body. Rods are then engaged between the screws in the superior and inferior vertebral bodies. Normally two screws are placed in each body. Therefore two rods are needed between the vertebrae. The rods are threaded at their ends to allow compression and distraction. However, the loads are born solely by the vertebral bodies. The posterior column of the spine or pedicle do not share any loads.

U.S. Pat. No. 4,289,123 discloses another anterior spinal fixation system, marketed by Zimmer, for treating tumors or thoracolumbar burst fractures. This system is similar to the Kanada device in that it uses rods between the superior and inferior vertebrae. In addition, a pair of large plates are contoured in accordance with the vertebrae and engage with the same through, such as screws.

Several plating systems have been developed for anterior internal fixation of the spine. Among these plating systems, the Syracuse I-plate provides a number of differently sized I-shaped plates which are engaged across the burst fracture. However, the Syracuse I-plate does not allow for compression or distraction of a bone graft between the superior and inferior vertebrae. The Stafix plating system, provided by Duma International of Taipai, Taiwan, includes a plate that has a number of screw holes and a single screw slot. The Stafix plate permits quadrilateral placement of bone screws, but not compression or distraction. Moreover, the Stafix plate, as with the above-mentioned anterior plates, can not provide rigid or semi-rigid fixation using bone screws or bone bolts. Moreover, U.S. Pat. No. 5,324,290 discloses an internal anterior fixation systems for treating vertebral burst fractures. The internal anterior fixation system uses an elongated plate which includes integral superior, inferior and bridge portions. The superior and inferior portions are provided for fixation to corresponding vertebrae while the bridge portion spanning between the portions over the affected vertebra.

Therefore, it is an object of the present invention to provide a fixation system that is capable of efficient management of thoracolumbar burst fractures and tumors and of easy implantation, to thereby reduce operative morbidity. Another object is to provide a system which permits anterior load sharing by the fixation system, posterior load sharing by posterior vertebral structure. Yet another object is to provide a fixation system that has compression and/or distraction function.

SUMMARY OF THE INVENTION

The present invention relates to an anterior transpedicular fixation system having longitudinal and transverse support members. The support members are connected to each other and mounted onto one or more vertebrae to support the spine and to prevent rotational or translational movement of the support members. The anterior transpedicular spinal fixation system allows a surgeon the full access to the disc area, captures two cortical surfaces via transpedicular screws or rods insertion, and pulls the two vertebral bodies closer to each other insuring a tight fusion. Therefore, the anterior transpedicular spinal fixation system is capable of distributing compressive loads to the support members, the vertebral body, and the posterior column of the spine, restraining the support members from rotational and translational movement, and preventing displacement of the graft material.

In one embodiment, the anterior transpedicular fixation system comprises a pair of supporting plates each having a first engaging portion, a second engaging portion, and a bridge portion integrally spanning between the first and second engaging portions. The first and second engaging portions each define a receiving portion, such as an opening.

Moreover, a plurality of fixation elements are provided each adapted to extend through one the openings and be mounted onto a vertebra. Further, the anterior transpedicular spinal fixation system comprises a joining member adapted to connect the bridge portions of the supporting plates. It is preferred that the components of the anterior transpedicular spinal fixation system are made of rigid materials. As a result, the supporting plates are restrained from rotational or translational movement. In an alternative embodiment, the bridge portions of the supporting plates and the clamping member are merged into one unitary member to provide both longitudinal and transverse support to the spine.

The present invention also relates to a method for maintaining vertebrae in a desired relationship. The surgical process according to the present invention includes removing the patient's intervertebral disc or vertebral body, inserting the bone graft material to replace the extracted anterior column, pre-drilling pilot screw holes on both cordices of the pedicle and the vertebral body, and mounting a support member to the vertebral body to increase its mechanical stability and to distribute rotational and translational loads to the support members, the vertebral body, and the posterior column of the spine.

These and other features and advantages of the present invention will be readily apparent from the following detailed description of the invention, the scope of the invention being set out in the appended claims.

BRIEF DESCRIPTION OF THE DRAWINGS

The detailed description of the present invention will be better understood in conjunction with the accompanying drawings, wherein like reference characters represent like elements, as follows.

DETAILED DESCRIPTION OF PREFERRED EMBODIMENTS

Exemplary anterior transpedicular fixation systems embodying the principles of the present invention are shown throughout the drawings. The anterior transpedicular fixation system of the present invention is adapted to be mounted onto one or more vertebrae to support the spine and to prevent the same from rotational or translational movement. In the following description of various embodiments of anterior transpedicular fixation systems, similar elements or components thereof are designated with reference numbers that have the same last two digits and redundant description is omitted.

Figure 1:
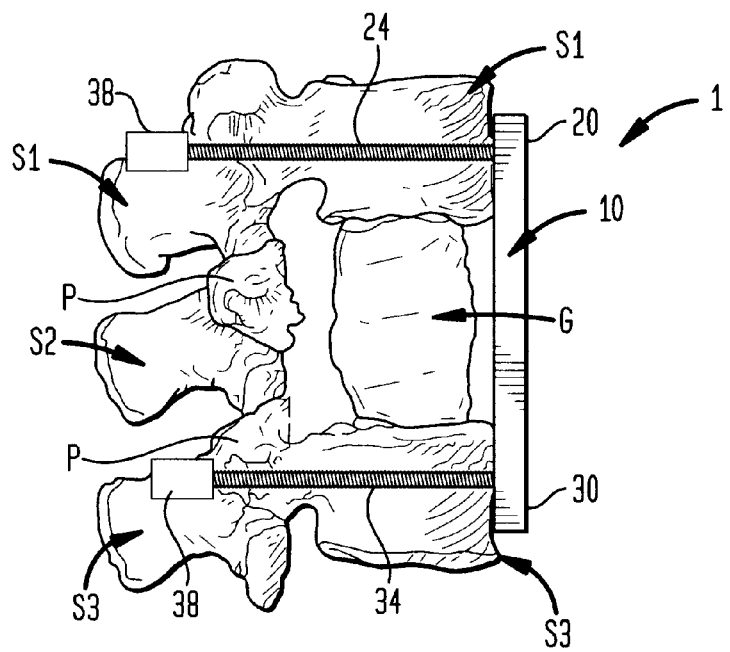
FIG. 1 is a lateral diagrammatic view of one embodiment of the spinal anterior fixation system of the present invention, mounted on a portion of a spinal column.

FIGS. 1 to 8 illustrate a first embodiment of the anterior transpedicular fixation system 1 formed according to the present invention. The anterior transpedicular fixation system 1 has a support member 10 adapted to span at least one vertebra and to be mounted thereonto. In an exemplary embodiment as shown in FIG. 1, the fixation system 1 includes a pair of supporting plates 10a and 10b adapted to span one or more vertebrae. For example, the supporting plates 10a and 10b can span a vertebra S2 that can have a burst fracture or tumors and can have been subjected to a vertebral body corpectomy. Additionally or alternatively, the fixation system 1 can apply to situations where a vertebral bone graft is inserted between first and second vertebrae, such as superior and inferior vertebrae S1 and S3 (see FIG. 1). The supporting plates 10a and 10b can be joined to each other through a joining member 80 and be mounted onto first and second vertebrae, respectively, through fixation elements 24 and 34. Preferably, the various components of the present invention are made of rigid material. As a result, the anterior transpedicular fixation system 1 of the present invention is capable of providing support for the spine. As the supporting plates 10a and 10b can be formed similarly, only one of which will be described in great detail as follows.

The supporting plate 10a can comprise first and second engaging portions 20 and 30 provided at opposite ends of the supporting plate 10a and a bridge portion 40 joining the first and second engaging portions 20 and 30. The first engaging portion 20, such as a superior engaging portion, can include a first receiving portion 22 for receiving a first fixation element 24. The first receiving portion 22 can be formed in various ways as will be described below. The first fixation element 24 can be adapted to engage with a first vertebra S1 to thus mount the first engaging portion 20 of the supporting plate 10a onto the first vertebra S1 as will be described below. Similarly, the second engaging portion 30, such as an inferior engaging portion, can include a second receiving portion 32 for receiving a second fixation element 34. The second receiving portion 32 can be formed in various ways as will be described below. The second fixation element 34 can be adapted to engage with the second vertebra S3 to thus mount the second engaging portion 30 of the supporting plate 30 onto the second vertebra S3 as will be described below.

The first and second receiving portions 22 and 32 can be formed in various ways to facilitate their engagement with the fixation elements 24 and 34, respectively. For instance, the receiving portions 22 and 32 can be threaded openings adapted to engage with plate thread portions 28 on the fixation elements 24 and 34. It will be appreciated that other embodiments for engaging the receiving portions 22 and 32 with the fixation elements 24 and 34 are also within the scope of the present invention.

Figure 4:
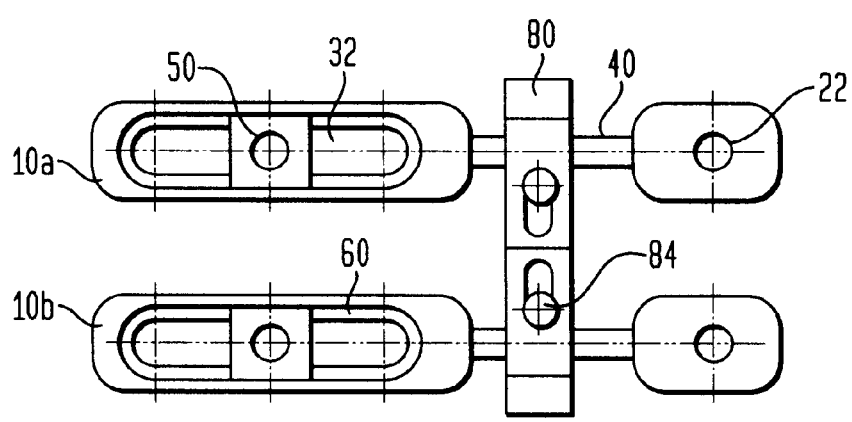
FIG. 4 is an elevational view of the supporting plates of the spinal fixation system of FIGS. 1 to 3, which supporting plates are joined by a clamping member.
Figure 5:
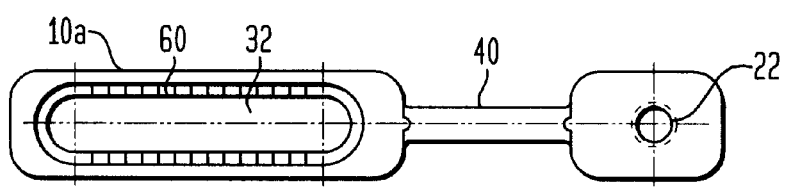
FIG. 5 is an elevational view showing one embodiment of a supporting plate of FIG. 4.

The supporting plate 10a can be formed so that it can be applied to various spinal anatomy situations and/or span different numbers of vertebrae. In an embodiment as shown in FIGS. 4 and 5, the second receiving portion 32 of the supporting plate 10a can be formed as an elongated slot. The second fixation element 34 can extend through and move along the second receiving portion 32 to a desired position depending on the spinal anatomy situations and/or the number of vertebrae that the supporting plate 10a spans. The second fixation element 34 can then be fixed to the second receiving portion 32 at the desired position through the mechanism discussed below. As a result, the elongated slot 32 is capable of allowing the supporting plate 10a to span a desired number of vertebrae and thus to fit for various spinal anatomy situations.

Figure 3:
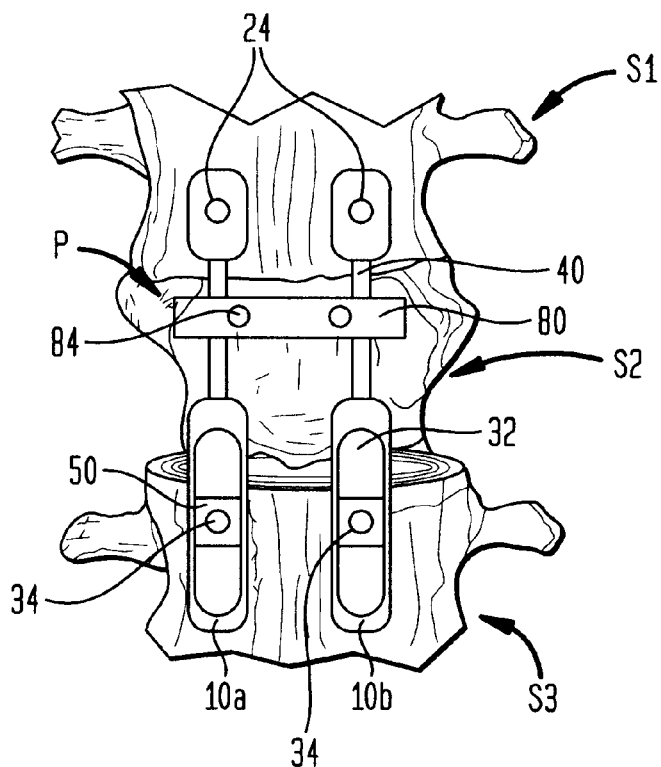
FIG. 3 is an anterior diagrammatic view of the spinal fixation system as illustrated in FIGS. 1 and 2, which is held in a desired position.

The elongated slot 32 of the supporting plate 10a can be formed in various ways. In one embodiment as shown in FIGS. 3 to 5, the longitudinal axis of the elongated slot 32 extends parallelly to that of the supporting plate 10a.

In one embodiment, the elongated slot 32 can further include a scalloped structure 60 provided thereon. Preferably, the scalloped structure 60 is provided at the interface of the elongated slot 32 and the fastener member 50, which can include a complementary scalloped structure 54 as will be described below. In a preferred embodiment, the scalloped structure 60 may be curved to engage a curved scalloped surface 56 on the fastener member 50 as will be described below. The elongated slot 32 and/or the scalloped structures 54 and 60 are capable of assisting the application of compression and/or distraction to the vertebrae after the fixation system 1 is partially mounted onto the vertebrae. In an exemplary embodiment, the scalloped slots 32 can allow the fixation elements 34 to be adjusted, oriented, and/or repositioned therein as desired to maintain an appropriate degree of compression or distraction at the fracture or graft site. It will be appreciated that minimizing the distance between the fixed vertebrae is essential to create compression on a bone graft G inserted between the vertebrae as shown in FIG. 1.

The supporting plate 10a of the anterior transpedicular fixation system 1 can have any suitable length. Among other factors, the length of the supporting plate 10a can be determined according to the spinal anatomy situations and/or the number of vertebrae that the supporting plate 10a spans. For example, the length of the supporting plate 10a can be between 6 cm and 12 cm. In one embodiment, a plurality of supporting plates 10a are formed which are in 1 cm increments.

The first and second engaging portions 20 and 30 can be joined to each other through a bridge portion 40. The bridge portion 40 can be configured to span a burst fracture vertebra S2. In a preferred embodiment, the bridge portion 40 can be so formed that its length can be adjusted as desired depending upon the particular vertebral anatomy. As shown in FIGS. 3 and 4, the distance between the first and second engaging portions 20 and 30 can be adjusted by changing the length of the bridge portion 40. It will be appreciated that various embodiments of bridge portion 40 are within the scope of the present invention.

In a preferred embodiment, the transverse width of the bridge portion 40 is smaller than the width of the first and second engaging portions 20 and 30 of the supporting plate 10a. Unlike conventional anterior plates, the supporting plate 10a of the present invention is capable of limiting its wider portions to the areas that directly interface the vertebrae. The reduced profile of the bridge portion 40 can facilitate the insertion of the supporting plate 10a and thus minimize possible trauma to surrounding tissue without affecting the stability of the supporting plate 10a in maintaining the fixation of the region.

The anterior transpedicular fixation system 1 of the present invention further comprises first and second fixation elements 24 and 34 adapted to mount the supporting plates 10a and 10b onto the vertebrae, respectively. As the fixation elements 24 and 34 can be formed similarly, only one of which will be described in great detail as follows.

Figure 2:
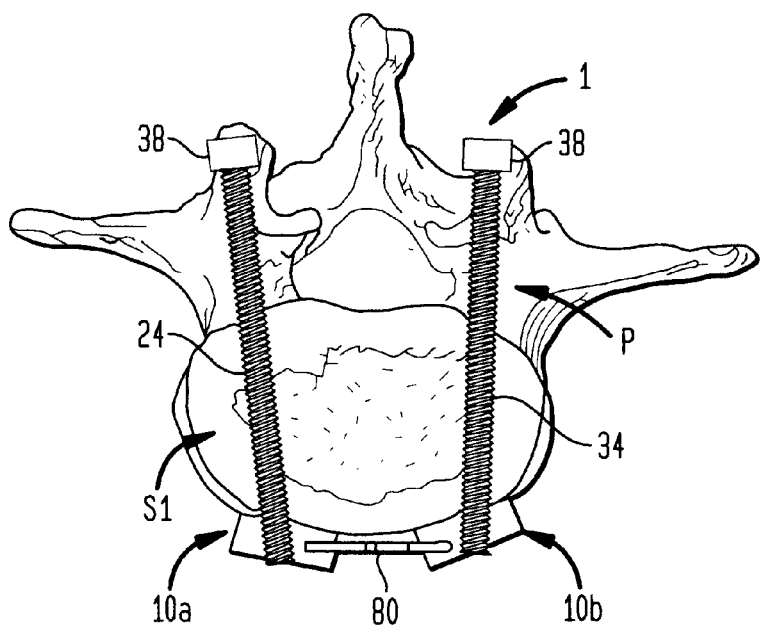
FIG. 2 is a top view of the spinal fixation system of the present invention of FIG. 1, which conforms to the transpedicular of the spine.
Figure 6:
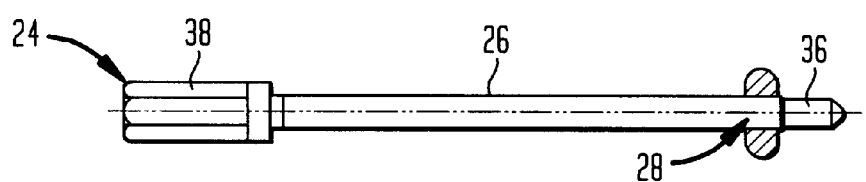
FIG. 6 is an elevational view of one embodiment of a transpedicular screw of FIGS. 1 to 3.
Figure 7A:
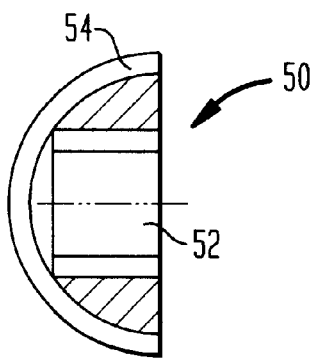
FIGS. 7a and 7b are transverse cross-sectional and elevational views of a fastener member of FIGS. 3 and 4.
Figure 7B:
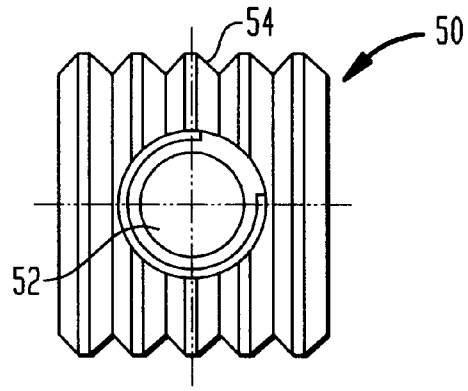
Figure 8A:
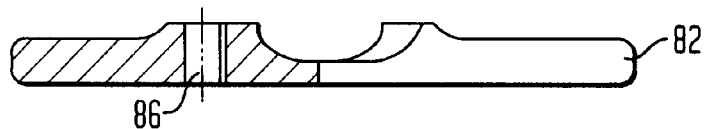
FIGS. 8a and 8b are longitudinal partial cross-sectional and elevational views of a clamping member of the fixation system of FIG. 4.
Figure 8B:
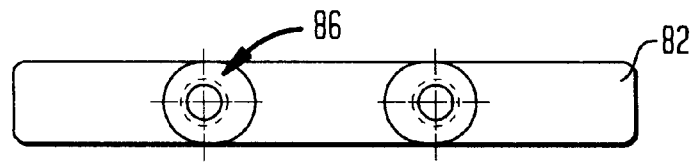

The fixation element 24 can be formed in various ways. In one embodiment, the fixation element 24 can be a transpedicular screw element. The transpedicular screw element 24 can be adapted to extend through the first and second thread openings 22 and 32 on the supporting plates 10a and 10b and further engage with the vertebrae. In an exemplary embodiment as shown in FIGS. 1, 2, and 6, the transpedicular screw element 24 can have the dual-threading design and include a bone screw thread 26 and a plate screw thread 28. The bone screw thread 26 can be used to purchase of bone and therefore can have a wider pitch and a deeper thread than those of the plate screw thread 28. The plate screw thread 28 can be adapted to engage with a thread opening 22 (see FIGS. 4 and 5) in the supporting plate 10a. In an alternative embodiment, the plate screw thread 28 can be adapted to engage with a threaded opening 32 in the fastener member 50. It will be appreciated that other embodiments of fixation elements 24 and 34 are within the scope of the present invention.

In the above embodiment, the transpedicular screw element 24 can have a drill bit end 36 as shown in FIG. 6. The drill bit end 36 can guide the transpedicular screw element 24 through the verteba and can be removed after the transpedicular screw element 24 is threaded into the supporting plate 10a. At the other end of the transpedicular screw element 24, a locking member 38, such as a locking nut (see FIG. 6), or similar locking devices is provided. The locking member 38 can engage with the posterior surface of the vertebrae column after the transpedicular screw element 24 is inserted into vertebra and mounted to one of the first and second engaging portions 20 and 30 as shown in FIGS. 1 and 2. Because the pedicle is the strongest vertebral structure, the anterior transpedicular fixation system 1 of the present invention allows loads to be distributed between and shared by the pedicles P and the supporting plates 10a and 10b.

In another embodiment, the fixation element 24 can further comprise a fastener member 50. The fastener member 50 can be adapted to mount the fixation element 24 onto the second receiving portion 32. In an exemplary embodiment, the fastener member 50 can have a threaded opening 52 for engaging with plate thread portions 28 on the fixation elements 24 and 34.

Additionally or alternatively, the fastener member 50 can have a scalloped structure 54 (see FIGS. 7a and 7b) for engaging with a complementary scalloped structure 60 on the second receiving portion 32 of the supporting plate 10a. In an exemplary embodiment, the scalloped structure 54 can be curved, such as that shown in FIGS. 7a and 7b. In a preferred embodiment, the curved scalloped structure 54 is a semi-circular surface. The scalloped structures 54 and 60 allow the fastener member 50 to be adjusted and oriented in the second receiving portion 32 as desired when applying compression and/or distraction to the vertebrae. It will be appreciated that other embodiments of the fastener member 50 are also within the scope of the present invention.

The anterior transpedicular fixation system 1 of the present invention further comprises a joining member 80 adapted to join the supporting plates 10a and 10b. The length of the clamping member 80 can be varied to accommodate different width of the vertebrae of patients. The joining member 80 can be formed in various ways. In an exemplary embodiment, the joining member 80 can be a two-piece clamping member include two half members 82, as illustrated in FIGS. 3, 4, 8a, and 8b. The two-piece joining member 80 can be adapted to join each other by various conventional clamping mechanism, such as clamping screws 84.

As shown in FIG. 4, the two half members 82 are adapted to sandwich the bridge portions 40 of the supporting plates 10a and 10b. Each half member 82 can have at least one screw opening 86 thereon for receiving the clamping screws 84. By tightening the clamping screws 84, the supporting plates 10a and 10b can be clamped and fixed in relation to each other and thus restrained from rotational and translational movement. Accordingly, the joining member 80 can form a stable, firm, and symmetrical structure, which allows optimum anterior load distribution between the joined vertebrae and the supporting plates 10a and 10b. It will be appreciated that other embodiments of the joining member 80 are also within the scope of the present invention.

The anterior transpedicular system 1 of the present invention can be made of any suitable material. Preferably, the material forming the anterior transpedicular system 1 is a material that is bio-compatible. Additionally or alternatively, the material can have the required stiffness for anterior fixation of the spine. Exemplary materials can be FDA approved human implant metals (e.g., 316L stainless steel), titanium, and titanium alloy (e.g., titanium-vanadium-aluminum). It will be appreciated that other applicable materials are also within the scope of the present invention.

In a typical surgical procedure, the fixation elements 24 and 34 are inserted into and through a patient's vertebae. Then the fixation elements 24 and 34 are made to extend through and partially engage with the receiving portions 22 and 32 of the supporting plates 10a and 10b. After applying compression and/or distraction to the supporting plates 10a and 10b, the fixation elements 24 and 34 can be completely joined with the receiving portions 22 and 32 to fix the supporting plates 10a and 10b to the patient's vertebrae, thereby forming a solid fixation. In the embodiment where transpedicular screws are used as the fixation elements 24 and 34, such transpedicular screws are inserted into a patients vertebae and the threaded holes 22 and 32 in the supporting plates 10a and 10b. Before the transpedicular screws 24 and 34 are to be firmly tightened, compression and/or distraction is applied to the supporting plates 10a and 10b.

Figure 9:
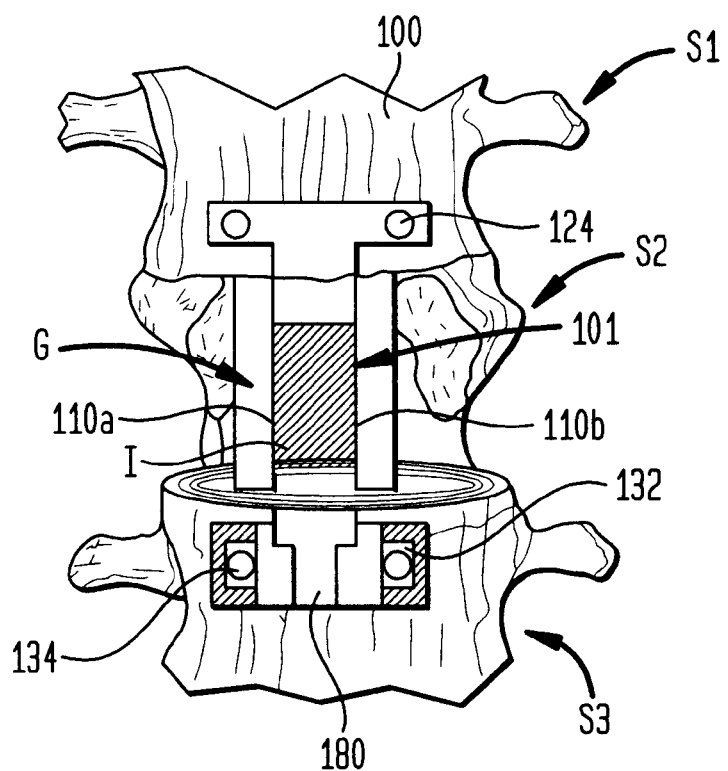
FIG. 9 is an anterior diagrammatic view of an alternative embodiment of the anterior spinal fixation system of the present invention, in which the supporting plates and the clamping member are integrated into a unitary member.

FIG. 9 shows an alternative embodiment of the anterior transpedicular system of the present invention. In the following description, elements or components similar to those in the embodiment of FIGS. 1 to 8, are designated with the same reference numbers increased by 100 and redundant description is omitted.

According to the anterior transpedicular fixation system 101, the supporting plates 110a and 110b are integrated with the joining member 180 to form a unitary member. As a result, the anterior transpedicular fixation system 101 comprises longitudinal and transverse support members 110 and 180 that are integrally formed. The longitudinal support member 110 is adapted to span at least one vertebra. The transverse support member 180 is adapted to accommodate different width of the vertebrae of patients. The anterior transpedicular fixation system 101 also comprises a plurality of fixation elements 124 and 134 adapted to mount the anterior transpedicular fixation system 101 onto a patient's vertebae. It is preferred that the various components of the anterior transpedicular fixation system 101 are made of rigid materials. Accordingly, the anterior transpedicular fixation system 101 of the present invention is capable of supporting the spine and preventing vertebrae from rotational or translational movement.

It will be appreciated that the various features described herein can be used singly or in any combination thereof. Therefore, the present invention is not limited to only the embodiments specifically described herein. While the foregoing description and drawings represent a preferred embodiment of the present invention, it will be understood that various additions, modifications and substitutions can be made therein without departing from the spirit and scope of the present invention as defined in the accompanying claims. The presently disclosed embodiment is therefore to be considered in all respects as illustrative and not restrictive, the scope of the invention being indicated by the appended claims, and not limited to the foregoing description.

We claim:

1. An internal anterior transpedicular fixation system for treating spinal pathologies including vertebral burst fractures or tumors which have been subjected to a vertebral corpectomy, comprising:

a pair of supporting plates, each plate for spanning at least one vertebra and having a first engaging portion, a second engaging portion, and a bridge portion joining said first and second engaging portions, said first engaging portion defining a first receiving portion, said second engaging portion defining a second receiving portion;

a clamping member for connecting said bridge portions of said supporting plates; and a plurality of fixation elements for mounting one of said first and second receiving portions onto a vertebra, wherein said fixation element is a transpedicular screw having a pointed tip, a bone screw thread portion in a middle portion of the screw and a plate screw thread portion adjacent to the pointed tip of the screw, said plate screw thread portion for engaging with said threaded opening in one of said first and second receiving portions;

whereby said supporting plates and the vertebra are restrained from relative rotational or translational movement.

2. The internal anterior fixation system of claim 1, wherein said first and second engaging portions each have a width, and said bridge portion has a width substantially less than the width of said first and second engaging portions.

3. The anterior fixation system of claim 1, wherein at least one of said first and second receiving portions is a threaded opening.

4. The anterior fixation system of claim 1, wherein said supporting plate includes a scalloped structure defined in at least one of said first and second receiving portions.

5. The anterior fixation system of claim 1, wherein said second receiving portions are elongated slots.

6. The anterior fixation system of claim 1, wherein said bone screw thread portion has a wider pitch and a deeper thread to purchase of bone.

7. The anterior fixation system of claim 1, wherein said transpedicular screw has a locking member provided at the opposite end of said plate screw thread portion for engaging said transpedicular screw onto the posterior surface of the vertebra.

8. The anterior fixation system of claim 1, wherein said fixation element further comprises a fastener member for engaging said plate screw thread portion on the transpedicular screw.

9. The anterior fixation system of claim 1, wherein said clamping member has an adjustable length.

10. An internal anterior transpedicular fixation system comprising:

a support member defining a plurality of engaging portions thereon, at least two of said engaging portions being spaced longitudinally from each other and for spanning at least one vertebra, at least two of said engaging portions being spaced laterally from each other and for spanning a lateral distance of said vertebra; and a plurality of fixation elements for mounting said engaging portions onto said vertebra, wherein said fixation element is a transpedicular screw having a pointed tip, a bone screw thread portion in a middle portion of the screw and a plate screw thread portion adjacent to the pointed tip of the screw;

whereby said support members and said vertebra are restrained from relative rotational or translational movement.

11. The internal anterior fixation system of claim 10, wherein said support member comprises first and second engaging portions for spanning at least two vertebrae and third and fourth engaging portions laterally spaced from said first and second engaging portions, respectively.

12. The internal anterior fixation system of claim 10, wherein at least one of said engaging portions is a threaded opening for engaging with said plate screw portion on one of said fixation elements.

13. The internal anterior fixation system of claim 10, wherein at least one of said fixation members further comprises a fastener member adapted to join said fixation element with one of said engaging portions, and wherein said fastener member includes a threaded opening for engaging with said plate screw portion on said fixation element.

14. The internal anterior fixation system of claim 10, wherein each said fixation element has a locking member at the opposite end of said plate screw portion.

15. A method for supporting vertebrae, comprising:

providing a fixation system comprising a support member and a plurality of fixation elements, said support member having first and second engaging portions for engaging with said fixation elements and for mounting onto at least one vertebra and said fixation element is a transpedicular screw having a pointed tip, a bone screw thread portion in a middle portion of the screw and a plate screw thread portion adjacent to the pointed tip of the screw;

forming a plurality of openings in the posterior surface bicortically of a displaced vertebra for receiving said fixation elements;

inserting said fixation elements from posterior vertebra bicortically into said openings respectively; and fixing said first and second engaging portions to their corresponding fixation elements to thereby support the vertebra.

16. The method of claim 15 further comprising:

fixing one of said first and second engaging portions; and applying compression or distraction to the vertebra before fixing the other of said first and second engaging portions.

17. The method of claim 15, wherein said support member comprises a pair of supporting plates, each having a first engaging portion and second engaging portion, the method further comprising joining said supporting plates by a clamping member to thereby hold said supporting plates against axial and rotational movement.

18. The method of claim 17 further comprising:

fixing one of said first and second engaging portions;

applying compression or distraction to the vertebra before fixing the other of said first and second engaging portions; and joining said supporting plates by clamping member after applying compression or distraction to the vertebra.

* * * * *